(12) United States Patent
Ho et al.

(10) Patent No.: US 7,560,283 B2
(45) Date of Patent: Jul. 14, 2009

(54) STORAGE-STABLE CELLULAR WHOLE BLOOD COMPOSITION CONTAINING ELEVATED AMOUNTS OF D-DIMER

(75) Inventors: Timothy Ho, Foothill Ranch, CA (US); Sholeh Zaminasli, Mission Viejo, CA (US); James Cole, Yorba Linda, CA (US); Alireza Ebrahim, Laguna Niguel, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 364 days.

(21) Appl. No.: 11/342,014

(22) Filed: Jan. 27, 2006

(65) Prior Publication Data

US 2007/0178168 A1 Aug. 2, 2007

(51) Int. Cl.
G01N 31/00 (2006.01)

(52) U.S. Cl. ...................................... 436/15
(58) Field of Classification Search ................. None
See application file for complete search history.

(56) References Cited

U.S. PATENT DOCUMENTS

| | | | |
|---|---|---|---|
| 3,553,310 A | 1/1971 | Csizmas et al. |
| 3,987,159 A | 10/1976 | Spona et al. |
| 4,102,810 A | 7/1978 | Armstrong |
| 4,341,527 A | 7/1982 | Zander et al. |
| 4,829,011 A | 5/1989 | Gibbons |
| 5,086,002 A | 2/1992 | Hillyard et al. |
| 5,413,913 A | 5/1995 | Hillyard et al. |
| 6,143,510 A | 11/2000 | Hoshino et al. |
| 2002/0106708 A1 | 8/2002 | Thomas et al. |
| 2005/0175977 A1 | 8/2005 | Posner et al. |
| 2006/0194272 A1 | 8/2006 | Okuda et al. |

OTHER PUBLICATIONS

Ilveskero, S., et al., "Procoagulant activity on platelets adhered to collagen or plasma clot," 2001, *Aterioscler. Thromb. Vasc. Biol.*, vol. 21, pp. 628-635.
Triplett, Douglas A., "Coagulation and bleeding disorders: review and update," 2000, *Clinical Chemistry*, vol. 46(8B), pp. 1260-1269.
Edwards, Patrick B. et al.; "D-Dimer Testing in the Diagnosis of Acute Venous Thromboembolism"; 1999, *Thrombosis and Haemostasis*, vol. 82, No. 2, pp. 688-694.
Ginsberg, Jeffrey S. et al.; Sensitivity and Specificity of a Rapid Whole-Blood Assay for D-Dimer in the Diagnosis of Pulmonary Embolism; 1998, *Ann Intern Med.*, vol. 129, pp. 1006-1011.
John, M.A. et al.; "The SimpliRED D Dimer Test: A Novel Assay for the Detection of Crosslinked Fibrin Degradation Products in Whole Blood"; 1990, *Thrombosis Research*, vol. 58, pp. 273-281.
Lee, Agnes Y.Y. et al.; "Clinical Utility of a Rapid Whole-Blood D-Dimer Assay in Patients with Cancer Who Present with Suspected Acute Deep Venous Thrombosis"; 1999, *Ann Intern Med.*, vol. 131, pp. 417-423.
Mayer, W. et al.; "Whole-blood immunoassay (SimpliRED®) versus plasma immunoassay (NycoCard™) for the diagnosis of clinically suspected deep vein thrombosis"; 1997, *VASA*, vol. 26, pp. 97-101.
Owings, John T. et al.; "Whole Blood D-Dimer Assay: An Effective Noninvasive Method to Rule Out Pulmonary Embolism"; 2000, *The Journal of Trauma, Injury, Infection, and Critical Care*, vol. 48, No. 5, pp. 795-800.
Rylatt, Dennis B. et al.; "A rapid whole-blood immunoassay system"; 1990, *The Medical Journal of Australia*, vol. 152, pp. 75-77.
Stein, Paul D. et al.; "D-Dimer for the Exclusion of Acute Venous Thrombosis and Pulmonary Embolism"; 2004, *Annals of Internal Medicine*, vol. 140, No. 8, pp. 589-607.
Wells, Philip S. et al.; "A Novel and Rapid Whole-Blood Assay for D-Dimer in Patients with Clinically Suspected Deep Vein Thrombosis"; 1995, *Circulation*, vol. 91, No. 8, pp. 2184-2187.
Wells, Philip S. et al.; "SimpliRED D-dimer can reduce the diagnostic tests in suspected deep vein thrombosis"; 1998, *The Lancet*, vol. 351, pp. 1405-1406.
Wells, Philip S. et al.; "Evaluation of D-Dimer in the Diagnosis of Suspected Deep-Vein Thrombosis"; 2003, *The New England Journal of Medicine*, vol. 349, No. 13, pp. 1227-1235.
Wuillemin, W.A.; "SimpliRED D-dimer Assay: Comparability of Capillary and Citrated Venous Whole Blood, Between-assay Variability, and Performance of the test for Exclusion of Deep Vein Thrombosis in Symptomatic Outpatients"; 1998, *Thromb Haemost*, vol. 79, pp. 1217-1219.
"Quantitative D-Dimer"; 2002, Alliance Laboratory Services: Update, 4 pages.
"Advanced D-Dimer Control Plasma"; 2000, Dade Behring, 1 page.
"Quality Control to Monitor Heart Disease Testing"; 2004, Bio-Rad Laboratories, 3 pages.
"D-Dimer"; http://www.labcorp.com/datasets/labcorp/html/chapter/mono/cf002900.htm, 3 pages, 2005.
"D-dimer: Lab Tests Online"; http://www.labtestonline.org/understanding/analytes/d_dimer/test.html, 3 pages, 2005.
"Kamiya Bioimedical Company"; http://www.kamiyabiomedical.com/03ClinicalDiagnosticsProducts/01Immunoassays/Rea..., 4 pages, 2005.
"D-Dimer: Lifting the Veil of Confusion"; http://www.beckman.com/resourcecenter/diagtoday/articles/features/betterddimer.asp, 2 pages, 2005.
"D-dimer"; http://www.diapharma.com/layout/set/print/content/view/full/638, 6 pages, 2005.
"D-Dimer: Facts & Figures"; http://npt.roche-diagnostics.com/content/products/d-dimer/facts_and_figures.html, 5 pages, 2005.
"d-dimer"; http://www.dadebehring.com/edbna2/ebusiness/search/searchResults.jsb?BV_SeccionID=@..., 6 pages, 2006.

(Continued)

*Primary Examiner*—Sandra E Saucier
(74) *Attorney, Agent, or Firm*—Townsend and Townsend and Crew LLP.; Henry Heines

(57) ABSTRACT

The present invention provides a cellular whole-blood D-dimer composition for use with diagnostic test procedures for D-dimer, and a method of its preparation. The composition comprises human erythrocytes and processed plasma to which D-dimer, and stabilizers, and optionally antimicrobial agents, are added and can be used as a standard and control for D-dimer testing.

48 Claims, No Drawings

OTHER PUBLICATIONS

"The STA Liatest Control"; Diagnostica Stago, 1 page, 2000.
"Liquichek D-dimer Control Levels 1, 2 and 3"; Bio-Rad, 6 pages, 2005.
"SimpliRED D-dimer"; Revision Mar. 2004, 2 pages.
"Clearview: simplify D-dimer"; 3 pages, 2006.
"STA Liatest Control N+P"; Diagno Stago; http://www.stago—us.com/pages/products.php?section=reagents&action=view&id=60, 1 page, 2006.
"Liquichek ToRCH Plus Controls"; http://www.medcompare.com/details/40821/Liquichek—ToRCH-Plus-Controls.html, 2 pages, 2006.
"Liquichek Hematology Control (A)"; http://www.medcompare.com/details/40824/Liquichek-Hematology-Control-(A).html, 2 pages, 2006.
"D-dimer Reference Centre"; http://www.agen.com/au/d-dimer/default.htm, 25 pages, 2005.
"D-dimer"; http://en.wikipedia.org/wiki/D-dimer, 3 pages, 2005.

STORAGE-STABLE CELLULAR WHOLE BLOOD COMPOSITION CONTAINING ELEVATED AMOUNTS OF D-DIMER

BACKGROUND OF THE INVENTION

This invention relates to method of preparation and applications of a liquid storage-stable cellular whole blood composition for use with diagnostic test procedures for D-dimer, which is routinely utilized as a biochemical marker to rule out deep vein thrombosis (DVT) and pulmonary embolism (PE).

Venous thromboembolism is a major health concern and occurs in a variety of diseases and causes significant mortality and morbidity. The most common manifestations of venous thromboembolism are deep vein thrombosis (DVT) and pulmonary embolism (PE). DVT is a blood clot (thrombus) that develops in one of the deep veins of the body, usually in the lower leg. It is a serious disorder that can lead to tissue damage, skin lesion, and even loss of the limb. PE is a condition in which a portion of the thrombus breaks loose and lodges in pulmonary arteries. PE may result in sudden death.

D-dimer molecules are the products of fibrin degradation. The presence of D-dimer in plasma at an increased concentration is proof that the fibrinolytic system (breakdown of fibrin clot) is in action in response to coagulation activation. Cutoff points for normal levels of D-dimer in human plasma will vary depending on factors such as gender and age, and may be different for different assay methods. Speaking very generally, therefore, a typical cutoff value for normal levels of D-dimer in human plasma will be from about 200 to about 500 ng/mL. Patients with venous thrombosis (DVT or PE) have significantly higher than normal levels of D-dimer in their blood. If the D-dimer level is significantly above the previously established cutoff value, then imaging procedures such as ultrasound and radiographic methods are performed to confirm that the patient has DVT or PE. Also, other possible causes of elevated D-dimer levels such as cancer, diabetes, trauma, cardiovascular disorders, and hematoma may be investigated. If the D-dimer level is below the cutoff value, then DTV and PE are ruled out, and the patient would not be sent for imaging studies or treated with anticoagulants. Thus, determination of D-dimer levels can be used both as a diagnostic tool and as a cost-savings tool in treatment of patients.

A number of diagnostic tests for D-dimer using different technologies have been described in the literature and introduced to the clinical laboratory market. For example, the Diagnostica Stago STA-LIATEST® D-DI, bioMerieux Vidas® D-Dimer, and Dade Behring Advanced D-Dimer assays are some of the quantitative test methods for determination of D-dimer in plasma. The Diagnostica Stago STA-LIATEST® D-DI is an immuno-turbidimetric assay using microlatex particles to which specific antibodies have been covalently attached. The Vidas® D-Dimer assay uses a two-step enzyme immunoassay sandwich method using enzyme linked fluorescent detection. The Dade Behring Advanced D-Dimer assay is also an immuno-turbidimetric assay. These all involve procedures for testing D-dimer content in plasma.

Unlike the above assays, several assays suitable for point-of-care settings have been introduced to the market for testing D-dimer in whole blood specimens. These, for instance, enable testing to be done at bedside or in a physician's office, with immediate results, rather than having the specimen sent to a laboratory to separate the plasma for testing. Two examples of such rapid qualitative assays for testing D-dimer in whole blood specimens are the SimpliRED® D-dimer assay from Agent Biomedical Ltd. (Australia) and the Clearview Simplify D-dimer assay from American Diagnostica, Inc. The SimpliRED® D-dimer assay is an autologous red cell agglutination assay. The active agent is a chemical conjugate of a monoclonal antibody specific to D-dimer linked to a monoclonal antibody, which binds to the red blood cell surface. The Clearview Simplify D-dimer assay is an immunochromatography test using D-dimer specific murine monoclonal antibody conjugated to colloidal gold particles to detect D-dimer. The antibody-gold-D-dimer complex migrates through a membrane in the aqueous phase until it is captured and concentrated at a zone to which a second D-dimer specific murine antibody has been bound. The concentration of the complexes at this zone causes a pink/purple line to appear on the membrane. In this assay, if D-dimer concentrations are below the clinically established cut-off, no visible line should appear.

Quality control materials are routinely used in clinical diagnostics laboratories to monitor the precision and accuracy of the clinical test methods and procedures, and this is done whether the assay is conducted in the laboratory or at the point of care of patients. For optimal performance, a quality control material should be as sensitive as the actual patient sample to the anticipated analytical variances. Furthermore, the quality control material should be storage-stable, and its analyte target concentrations should challenge the medical decision point of the assay. Other desirable features of a quality control material are low cost, lot-to-lot reproducibility, and ease of manufacturing.

In an early publication describing work on the SimpliRED assay [John et al., Thrombosis Research 58:273 (1990)], group O negative whole blood with D-dimer antigen added in serial dilutions to produce a series of concentrations was used as a control. However, the SimpliRED assay is marketed with plasma-based controls and the control marketed with the Clearview Simplify assay is only a "low molecular weight D-dimer spiking solution". Additionally, several plasma- and buffer-based D-dimer controls for testing this marker in plasma are currently available in the market. One, the Stago LIATEST® (D-Dimer Control (available from Diagnostica Stago, Asnieres-sur Seine, France) is a bi-level lyophilized control composed of citrated normal and abnormal human plasma for positive and negative levels, respectively. Another, the Dade Behring Advanced D-Dimer Control Plasma 1 and 2 (available from Dade Behring Inc., Deerfield Ill.) is a bi-level lyophilized control comprised of pooled plasma supplemented with a D-dimer preparation, stabilized with Hepes buffer, and preserved with Proclin. Bio-Rad Laboratories (Hercules, Calif.) offers a liquid plasma-based control containing three elevated levels of D-dimer prepared from processed human plasma and preservatives. At this time, however, there is no commercially available storage-stable cellular whole blood D-dimer composition for use as control or calibrator in D-dimer assays intended for whole blood testing.

There exists a need for a storage-stable cellular whole blood based quality control material for use with the D-dimer assays intended for whole blood testing. Such a product would be similar in nature to a patient sample and could be used directly on test materials that are designed for point-of-care testing in that it would not be necessary to separate blood cells from plasma in testing such samples. The present invention satisfies that need and meets the other essential requirements for a quality control material, such as responding the same way to analytical variances as a patient sample by using a combination of human erythrocytes and plasma as the base matrix, having target values that challenge the linear dynamic range of the assay, and providing acceptable opened-vial and closed-vial stabilities for long term use.

BRIEF SUMMARY OF THE INVENTION

In one aspect, this invention comprises a whole blood cellular composition that comprises defibrinated plasma having a pH of from about 4 to about 9 and a total protein content of from 0 to about 10 g/dL, erythrocytes, a stabilizer and an elevated level of D-dimer.

In a second aspect, this invention comprises a method of preparing a whole blood composition having an elevated level of D-dimer comprising combining a composition comprising erythrocytes and a stabilizer with a composition comprising defibrinated plasma having a pH of from about 4 to about 9 and a total protein content of from 0 to about 10 g/dL, and a sufficient amount of D-dimer to produce a product containing an elevated amount of D-dimer.

In a third aspect, the invention comprises a method of monitoring a whole-blood based D-dimer assay comprising using a composition as defined above, and preferably a series of two or more such compositions having different elevated amounts of D-dimer, as a control material.

This invention also comprises a control kit designed primarily for use in connection with whole-blood D-dimer assays comprising one or more of such compositions. If the kit comprises two or more such compositions, then the compositions have different elevated amounts of D-dimer.

DETAILED DESCRIPTION OF THE INVENTION

This invention involves using stabilized erythrocytes, processed plasma, and D-dimer (which may be native, synthetic, or recombinant D-dimer) along with stabilizers and preferably also antimicrobial agents to prepare compositions which can be used as standards, reference materials, and/or controls with diagnostic test procedures for determination of D-dimer in whole blood.

In general, the compositions are whole blood cellular compositions that comprise defibrinated plasma having a pH of from about 4 to about 9 and a total protein content of from 0 to about 10 g/dL, erythrocytes, a stabilizer and an elevated level of D-dimer. Preferably the compositions contain from about 10 to about 70, most preferably from about 40 to about 60 volume %, of a defibrinated plasma that likewise has a pH of from about 4 to about 9, preferably from about 5 to about 8 and most preferably from about 6 to about 7; a total protein content of from 0 to about 10 g/dL, preferably from about 4 to about 8, most preferably from about 5 to about 7 g/dL; from about 10 to about 70, preferably from about 30 to about 55, volume % of erythrocytes, from about 0.01 to about 10, preferably from about 0.1 to about 2.0 weight % of a stabilizer and an elevated amount of D-dimer with respect to endogenous D-dimer, preferably, up to about 200 µg/mL of a D-dimer. The inclusion of protein in the compositions is optional (i.e. the protein content could be 0) but preferably protein is present in the compositions is up to about 10 g/dL. Compositions containing such amounts of protein will more closely resemble whole blood. In a preferred embodiment the compositions also contain from about 0 to about 2, most preferably from about 0.01 to about 1 weight %, of one or more antimicrobial agents.

The plasma used in the compositions and methods of the invention is preferably human plasma, but may be other mammalian plasma such as bovine or porcine plasma, or it may be an artificial plasma prepared as known in the art and comprising an aqueous fluid with some constituents of human plasma such as electrolytes, albumin, buffer, etc. For use in the compositions, the plasma is processed by defibrination using techniques as known in the art to bring the fibrin content to below about 5 mg/dL. Then, the total protein content of the plasma is adjusted to a value of from about 0 to about 10, preferably from about 4 to about 8, and most preferably from about 5 to about 7 g/dL by any suitable technique, for instance by concentrating the composition or diluting it with plasma, serum, or isotonic neutral solution. The pH is then adjusted to a value of between about 4 and about 9, preferably between about 5 and about 8, most preferably between about 6 and about 7.

Following that, additional optional ingredients such as an enzyme inhibitor and one or more antimicrobial agents may be added. The endogenous D-dimer content of these compositions (which may also be called a "base matrix) is then determined.

The processed plasma prepared as just described is then combined with erythrocytes, preferably with packed erythrocytes, and a stabilizer (which may be included with the packed erythrocytes or added separately). The erythrocytes are preferably human erythrocytes but may alternatively be mammalian, or even avian, erythrocytes. Suitable non-human mammalian erythrocytes include porcine, bovine, caprine, equine and ovine erythrocytes. Suitable avian erythrocytes include chicken and turkey erythrocytes. The resulting composition will contain from about 10 to about 70, preferably from about 30 to about 55, volume % erythrocytes.

Purified or partially purified D-dimer, which may be native, synthetic or recombinant D-dimer, and is preferably human D-dimer, is then spiked into the composition to prepare compositions with different levels of this marker at below, near, and above the clinical decision point for D-dimer. A sample of the composition with no added D-dimer is used as the base value in a set of controls, and samples having differing amounts of spiked D-dimer are used as controls for the test. The term "elevated level" of D-dimer, as used herein, refers to a D-dimer content at least about 200 ng/mL above that of typical endogenous D-dimer and is achieved by the spiking of the composition, i.e., addition of an amount of D-dimer to produce a control composition that has a predetermined elevated D-dimer content. Other biochemical markers such as those used for cardiac risk and stroke assessments, for example Troponin I, CKMB (creatine kinase MB), BNP (B-type natriuretic peptide), hsCRP (high-sensitivity C-reactive protein), homocysteine, HDL (high-density lipoprotein), LDL (low-density lipoprotein), cholesterol, and pro-BNP (pro-B-type natriuretic peptide), may also be spiked in the compositions. Compositions having different elevated D-dimer contents are then filled and capped aseptically and refrigerated.

Stabilizers preferably are included in the erythrocyte composition, but may be added separately. Suitable stabilizers include inorganic stabilizers such as cyanide (e.g., as potassium cyanide) and ferricyanide (e.g., as potassium ferricyanide) ions and organic stabilizers such as protease inhibitors including serine protease inhibitors, and cross-linking agents such as formaldehyde and glutaraldehyde.

Preferably the compositions contain one or more antimicrobial agents. These are preferably incorporated into the processed plasma, but may be added separately to the compositions. Typically a combination of antimicrobial agents will be used in a given composition. Suitable antimicrobial agents include ciprofloxacin, chloramphenicol, gentamicin, amikacin, tobramycin, and amphotericin B.

Kits of the present invention comprise one or more compositions of the invention, optionally together with a composition of similar nature but which does not contain an elevated level of D-dimer. Kits for use in qualitative assays will typically contain a composition that has an elevated level of D-dimer ("positive sample") and one that does not ("negative sample"). Kits for quantitative assays typically contain three compositions—called "low", "medium" and "high" samples, where the medium and high samples contain different elevated levels of d-dimer and the low sample does not contain an elevated amount of D-dimer.

The invention is illustrated in a non-limiting manner by the following example, which includes a general method of preparing the compositions of this invention, together with a specific example of the compositions and their performance.

General procedure:

Preparation of Erythrocytes:

Human packed red blood cells (RBCs) are centrifuged for 20 min at 2500 RPM at 15° C. After centrifugation, the residual plasma containing anticoagulant is aspirated and the buffy coat on the top of packed cells removed. The cells are then re-suspended in equal volume of an isotonic solution containing 6.4 g/L of ethylenediaminetetraacetic acid (EDTA), 2.0 g/L MOPS, 0.4 g/L KFeCN, 0.2 g/L KCN, 0.5 g/L NaF, 80.0 g/L PEG, and 4.0 g/L $NaNO_3$. The re-suspended cells are then centrifuged again for 20 min at 2500 RPM at 15° C. After centrifugation, the suspension fluid is aspirated, and the cells are re-suspended in the suspension fluid and stored at 2-8° C. for 12 weeks to stabilize the cells.

After this incubation period, the stabilized RBCs are then centrifuged for 20 minuets at 2-8° C. and 2500 RPM. After removing the supernatant, the packed cells are re-suspended in an equal volume of a normal saline solution (0.85 g/L NaCl, pH =7.2), and the centrifugation step repeated once more. At the last centrifugation cycle, the supernatant is removed and the packed RBCs stored at 2-8° C. At this stage, the RBC count of the packed cells typically is >6×10$^6$ RBCs/μL.

Preparation of Processed Plasma:

Units of normal human plasma are pooled and defibrinated as known in the art. The total protein concentration of the resulting serum (referred to herein as the base matrix) is then adjusted to a value within the range of from 0 to about 10 g/dL, for instance, to 6.0 g/dL, by concentrating the base matrix or diluting it with normal saline solution. The pH of the base matrix is then adjusted to a value within the range of from about 4 to about 9, for example to a value of about 6.8-7.0. An enzyme inhibitor, aminoethyl benzenesulfonyl fluoride (AEBSF), is added to the base matrix at a final concentration of 30 mg/L. Also, antimicrobial agents (with typical values shown) such as ciprofloxacin (30 mg/L), chloramphenicol (100 mg/L), gentamicin (100 mg/L), amikacin (40 mg/L), tobramycin (30 mg/L), and/or amphotericin B (20 mg/L) may be added to the base matrix. The pH is again adjusted to the chosen value and the endogenous D-dimer in the base matrix is determined using a commercially available assay such as Stago Diagnostica STA-LIATEST D-DI assay. The concentration of the endogenous D-dimer in a typical preparation of the base matrix is typically less than 0.5 μg/mL fibrin equivalent units (FEU).

SPECIFIC EXAMPLE

A 40-80 μg/mL stock solution of D-dimer in defibrinated human plasma was prepared using native human D-dimer, by combining a base matrix prepared as above, which had a pH of 6.8-7.0 and a protein content of 6.0 g/dL to prepare an elevated D-dimer composition ("Positive Level" or "Level 2") having a D-dimer concentration of 36-44 μg/mL, i.e. a concentration above that of the clinical decision points of the two commercial assays (the cutoff point for D-dimer of the Agen SimpliRED Assay is 0.20 μg/mL; that of the Clearview Simplify Assay is 0.08 μg/mL). A similar composition ("Negative Level" or "Level 1") was prepared with no D-dimer added to the base matrix composition. Analyte concentrations were then determined after addition of spike solutions, and adjustments to analyte concentrations were made through re-spiking or dilution of the pool of D-dimer solutions in the base matrix compositions to ensure multi-level and clinical utility of the composition. The individual pools were then aseptically filtered through 0.2 μm filters and stored at 2-8° C.

Stabilized and concentrated erythrocytes prepared as above were then added to the individual pools to prepare suspensions of RBCs in processed plasma. The RBC count in the individual pools was adjusted to 3–5×10$^6$ RBC/μL. The individual pools were filled in the pre-sterilized small glass vials and closures, and stored at 2-8° C.

Performance of the Product:

Table 1 contains the recovery data for a typical pilot lot of the composition for use as a control for qualitative detection of D-dimer.

TABLE 1

Performance of the Product on Different Test Methods

| Test Method | Level 1 result | Level 2 result |
|---|---|---|
| SimpliRED ® D-dimer Assay | Negative | Positive |
| Clearview Simplify ™ D-dimer Assay | Negative | Positive |

The compositions thus performed appropriately.

Closed-vial storage stability of the product was evaluated by using an accelerated stability model to predict product shelf life. For this purpose, vials of the above product were stored at an elevated temperature (25° C.) for pre-determined periods of time to observe analyte decomposition/degradation (recommended storage temperature is 2-8° C.) and assayed for D-dimer at the end of various incubation periods. The results of these studies predicted that the product would be stable for at least 1 year when stored unopened at 2-8° C.

Opened-vial storage stability of the product was also evaluated by simulating actual use conditions by clinicians. This was done by storing the vials at 2-8° C. and removing them from the refrigerator every working day for 36 days, allowing the vials to equilibrate at room temperature for 15 minutes, opening the vials and exposing their contents to the laboratory environment, then closing the vials and returning them to storage at 2-8° C. Samples of the vials were assayed during this study. Table 2 shows the opened-vial stability results for D-dimer in pilot lots prepared, i.e. that the compositions continued to perform accurately. The results of this study indicate that the product will be stable for at least 36 days when opened and stored at 2-8° C.

TABLE 2

Opened-Vial Stability of the Composition at 2-8° C. Using SimpliRED ® D-dimer Assay

| Time (days) | Level 1 | Level 2 |
|---|---|---|
| 1 | Negative | Positive |
| 7 | Negative | Positive |
| 15 | Negative | Positive |

TABLE 2-continued

Opened-Vial Stability of the Composition at 2-8° C. Using SimpliRED ® D-dimer Assay

| Time (days) | Level 1 | Level 2 |
|---|---|---|
| 30 | Negative | Positive |
| 36 | Negative | Positive |

Other examples of this invention may use as stabilizers cross-linking reagents typically used for fixing erythrocytes such as glutaraldehyde and formaldehyde at high (2%) and low (0.01%) concentrations, to produce non-lysable and lysable erythrocyte preparations. Furthermore, animal blood, specifically, animal red blood cells, can be used to minimize the potential risk of exposure to human blood-borne pathogens.

Typically compositions according to the invention have a hematocrit value (HCT), the ratio of volume of erythrocytes to the total volume of blood, of 20 to 60% and a hemoglobin concentration (Hgb) of 5 to 17 g/dL.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A liquid composition for use as a control for an assay of D-dimer in the plasma of a human patient of specified gender and age and for a specified assay method comprising:
    a defibrinated plasma having a pH of about 4 to about 9 and a total protein content of proteins other than D-dimer of 0 to about 10 g/dL,
    erythrocytes,
    one or more stabilizers, and
    D-dimer concentration that is elevated with respect to a normal concentration of endogenous D-dimer content for said specified gender and age and said specified assay method, wherein the D-dimer concentration of the liquid composition is above 200 ng/ml.

2. A composition according to claim 1 wherein the erythrocytes are mammalian erythrocytes.

3. A composition according to claim 1 wherein the erythrocytes are human erythrocytes.

4. A composition according to claim 1 wherein the erythrocytes are avian erythrocytes.

5. A composition according to claim 1 wherein the erythrocytes are selected from human, porcine, bovine, equine, caprine, ovine, chicken and turkey erythrocytes.

6. A composition according to claim 1, wherein the D-dimer is selected from native, recombinant, and synthetic D-dimer.

7. A composition according to claim 1, wherein the D-dimer is human D-dimer.

8. A composition according to claim 1, wherein the plasma is selected from mammalian plasma and artificial plasma.

9. A composition according to claim 1, wherein the plasma is mammalian plasma.

10. A composition according to claim 1, wherein the plasma is human plasma.

11. A composition according to claim 1, wherein the plasma is artificial plasma.

12. A composition according to claim 1 further comprising one or more antimicrobials.

13. A composition according to claim 12 wherein the one or more antimicrobials are selected from ciprofloxacin, chloramphenicol, gentamicin, amikacin, tobramycin, and amphotericin B.

14. A composition according to claim 1 wherein the one or more stabilizers comprise a protease inhibitor.

15. A composition according to claim 14 wherein the protease inhibitor comprises a serine protease inhibitor.

16. A composition according to claim 1 wherein the one or more stabilizers comprise a cross-linking agent.

17. A composition according to claim 16 wherein the cross-linking agent comprises formaldehyde or glutaraldehyde.

18. A composition according to claim 16 wherein the cross-linking agent is present in a concentration of from about 0.01% to about 2%.

19. A composition according to claim 1 wherein the one or more stabilizers comprise cyanide ion or ferricyanide ion.

20. A composition according to claim 19 wherein the one or more stabilizers comprise potassium cyanide.

21. A composition according to claim 1 comprising from about 0.1 to about 2.0 weight % of one or more stabilizers.

22. A composition according to claim 1 wherein the erythrocytes are lysable erythrocytes.

23. A composition according to claim 1 wherein the erythrocytes are not lysable.

24. A composition according to claim 1 having a pH of from about 5 to about 8.

25. A composition according to claim 1 having a pH of from about 6 to about 7.

26. A composition according to claim 1 comprising from about 1 to about 80 volume % plasma.

27. A composition according to claim 1 comprising from about 40 to about 60 volume % plasma.

28. A composition according to claim 1 comprising from about 10 to about 70 volume % erythrocytes.

29. A composition according to claim 1 comprising from about 30 to about 55 volume % erythrocytes.

30. A composition according to claim 1 having a protein content of from about 4 to about 8 g/dL.

31. A composition according to claim 1 having a protein content of from about 5 to about 7 g/dL.

32. A composition according to claim 1 further comprising one or more cardiac risk assessment or stroke and coagulation markers.

33. A composition according to claim 32 wherein the markers are selected from Troponin I, CKMB, BNP, hsCRP, homocysteine, HDL, LDL, cholesterol, and pro-BNP.

34. A composition according to claim 1 having a hematocrit value of from about 20 to about 60%.

35. A composition according to claim 1 having a hemoglobin concentration of from about 5 to about 17 g/dL.

36. A method for preparing a liquid composition for use as a control for an assay of D-dimer in the plasma of a human patient of specified gender and age and for a specified assay method comprising: combining
    (a) a processed plasma comprising a defibrinated plasma having a pH of about 4 to about 9 and a total protein content of 0 to about 10 g/dL and
    (b) erythrocytes and one or more stabilizers and subsequently adding
    (c) D-dimer to elevate the D-dimer concentration of the liquid composition to above 200 ng/ml.

37. A method according to claim 36 wherein the erythrocytes are mammalian erythrocytes.

38. A method according to claim 36 wherein the erythrocytes are human erythrocytes.

39. A method according to claim 36 wherein the erythrocytes are avian erythrocytes.

40. A method according to claim 36 wherein the erythrocytes are selected from human, porcine, bovine, equine, caprine, ovine, chicken and turkey erythrocytes.

41. A method according to claim 36 wherein the D-dimer is selected from native, recombinant, and synthetic D-dimer.

42. A method according to claim 36 wherein the D-dimer is human D-dimer.

43. A method according to claim 36 wherein the plasma is selected from mammalian plasma and artificial plasma.

44. A method according to claim 36 wherein the plasma is human plasma.

45. A method according to claim 36 wherein the plasma is artificial plasma.

46. A method according to claim 36 wherein the composition further comprises one or more antimicrobials.

47. A method of monitoring a whole-blood based D-dimer assay comprising using a composition according to claim 1 as a control material.

48. A method according to claim 47 comprising using a series of two or more said compositions having different elevated amounts of D-dimer, as a control material.

* * * * *